(12) United States Patent
Lee

(10) Patent No.: US 11,612,671 B2
(45) Date of Patent: Mar. 28, 2023

(54) AROMA DIFFUSER

(71) Applicant: Puzhen Life Co., Inc., Shatin (HK)

(72) Inventor: Andy Lee, Shatin (HK)

(73) Assignee: PUZHEN LIFE CO., INC., Shatin (HK)

( * ) Notice: Subject to any disclaimer, the term of this patent is extended or adjusted under 35 U.S.C. 154(b) by 333 days.

(21) Appl. No.: 17/081,295

(22) Filed: Oct. 27, 2020

(65) Prior Publication Data
US 2022/0088253 A1 Mar. 24, 2022

(30) Foreign Application Priority Data
Sep. 21, 2020 (CN) .......................... 202010996650.1

(51) Int. Cl.
*A61L 9/03* (2006.01)
*A61L 9/012* (2006.01)

(52) U.S. Cl.
CPC .............. *A61L 9/03* (2013.01); *A61L 9/012* (2013.01); *A61L 2209/134* (2013.01)

(58) Field of Classification Search
CPC ...... A61L 9/03; A61L 9/012; A61L 2209/134; A61L 2209/11; A61L 2209/135; A61L 9/14; A61L 9/013; B05B 7/0416; B05B 12/0024
See application file for complete search history.

(56) References Cited

U.S. PATENT DOCUMENTS

| 5,888,059 | A | 3/1999 | Edwards et al. |
| 6,394,575 | B1 | 5/2002 | Kent |
| 9,511,166 | B1 * | 12/2016 | Li .................. B05B 7/2416 |
| 9,643,197 | B2 | 5/2017 | Bellandi |

FOREIGN PATENT DOCUMENTS

| CN | 101664726 A | 3/2010 |
| CN | 202061733 U | 12/2011 |
| CN | 103406220 A | 11/2013 |
| CN | 205833418 U | 12/2016 |
| CN | 110972465 A | 4/2020 |
| CN | 111111952 A | 5/2020 |
| JP | 2002320881 A | 11/2002 |
| JP | 2009039218 A | 2/2009 |

\* cited by examiner

*Primary Examiner* — Sean E Conley
*Assistant Examiner* — Brendan A Hensel
(74) *Attorney, Agent, or Firm* — Cantor Colburn LLP

(57) ABSTRACT

An aroma diffuser, including: an oil supply structure, provided with an oil storage bottle for containing essential oil and an oil delivery pipe connected to the oil storage bottle, the oil delivery pipe includes a liquid outlet, and an end side of the oil delivery pipe is provided with an atomizing space; and an air delivery structure, provided with a working mode and a wall-breaking mode, in the working mode, an atomizing airflow is generated, and a negative pressure is formed to force the essential oil to enter the atomizing space, in the wall-breaking mode, an impinging airflow and a buffering airflow are alternately generated, or a buffering airflow and an impinging airflow are alternately generated, the impinging airflow flows through the atomizing space and breaks through a surface tension of the essential oil, the buffering airflow flows through the atomizing space and takes the essential oil away.

12 Claims, 3 Drawing Sheets

```
                    ┌─────────────────────────────────┐
                    │   Triggering a working signal   │
                    └─────────────────┬───────────────┘
                                      ▼
  ┌──────────────────────────────────────────────────────────────┐
  │ Air delivery structure 20 starting a wall-breaking mode, air │
  │ delivery structure 20 alternatively generating an impinging  │
  │ airflow and a buffering airflow, or alternatively generating a │
  │       buffering airflow and an impinging airflow             │
  └──────────────────────────────┬───────────────────────────────┘
                                 ▼
  ┌─────────────────────────────────────────────┐        ┌──────────────────────────────┐
  │ Air delivery structure 20 starting a working │        │                              │
  │   mode after the wall-breaking mode ends,    │───────▶│ Triggering a wall-breaking   │
  │ generating an atomizing airflow to atomize   │        │           signal             │
  │             the essential oil                │        └───────────────┬──────────────┘
  └─────────────────────┬───────────────────────┘                        ▼
                        │                                 ┌──────────────────────────────┐
                        │                                 │ Air delivery structure 20    │
                        │                                 │ stopping a working mode,     │
                        ▼                                 │ starting a wall-breaking     │
  ┌─────────────────────────────────────────┐◀────────────│ mode, and continuing the     │
  │        Triggering a stop signal         │             │ working mode after the wall- │
  └─────────────────────┬───────────────────┘             │      breaking mode ends      │
                        ▼                                 └──────────────────────────────┘
  ┌──────────────────────────────────────────────────────┐
  │ Air delivery structure 20 stopping the working mode, │
  │   starting a sweeping mode, and generating a         │
  │               sweeping airflow                       │
  └──────────────────────────────────────────────────────┘
```

FIG. 4

AROMA DIFFUSER

CROSS-REFERENCE TO RELATED APPLICATION

This application claims priority to CN Invention Patent Application No. 202010996650.1, filed on Sep. 21, 2020, the content of which is incorporated herein by reference in its entirety.

TECHNICAL FIELD

The present application relates to the field of atomization technology, and more particularly to an aroma diffuser.

BACKGROUND

An aroma diffuser includes an oil supply structure and an air delivery structure. The oil supply structure includes an oil storage bottle configured for accommodating essential oil and an oil delivery pipe connected to the oil storage bottle. An end of the oil delivery pipe is an oil nozzle for the essential oil to flow out. The air delivery structure is configured to generate high-speed airflow. By using Venturi principle, the high-speed airflow generated by the air delivery structure passes by the oil nozzle, thereby forcing the essential oil in the oil storage bottle to flow out of the oil nozzle and mix with the high-speed airflow to produce an atomization effect. The space where the essential oil and the high-speed airflow are mixed is defined as the atomizing space.

During long-term use, the essential oil may deposit in the atomizing space and the oil delivery pipe to form a passivation layer. Normally, the oil storage bottle is placed vertically. When the oil nozzle is upward, the upper surface of the oil delivery pipe is prone to retain the essential oil, the essential oil accumulates on the upper surface of the oil delivery pipe for a long time to form a passivation layer, which increases the surface viscosity, and block the flow of airflow, thereby affecting the mixing of airflow and essential oil, resulting in poor atomization effect; the pipe wall of the oil delivery pipe is also prone to form passivation layer due to the residual essential oil, which increases the surface viscosity, and hinder the upward movement of the essential oil, under the action of the same high-speed airflow, the atomization effect becomes worse, even no fog is produced. What's more, the residual essential oil accumulates and blocks the oil delivery pipe, causing the aroma diffuser to fail to atomize the essential oil.

SUMMARY

The objective of the present application is to overcome the deficiencies of the prior art, an aroma diffuser is provided, which aims to solve the problem that the atomization effect of the existing aroma diffuser becomes worse after being used for a long time.

To achieve the above objective, the embodiments of the present application provide the following technical solution:

An aroma diffuser, includes:

an oil supply structure, including an oil storage bottle configured for containing essential oil and an oil delivery pipe connected to the oil storage bottle, the oil delivery pipe includes a liquid outlet for the essential oil to flow out, and an end side of the oil delivery pipe is provided with an atomizing space; and an air delivery structure, provided with a working mode and a wall-breaking mode, when the air delivery structure is in the working mode, an atomizing airflow is generated, the atomizing airflow passes by the liquid outlet, a negative pressure is formed at the liquid outlet, and the negative pressure forces the essential oil to enter the atomizing space; and when the air delivery structure is in the wall-breaking mode, an impinging airflow and a buffering airflow are alternately generated, or a buffering airflow and an impinging airflow are alternately generated, the impinging airflow flows through the atomizing space and breaks through a surface tension of the essential oil, the buffering airflow flows through the atomizing space, and the buffering airflow takes the essential oil in the atomizing space away from the atomizing space in the absence of forcing the essential oil in the oil storage bottle to move to the atomizing space.

Optionally, when the air delivery structure is in the wall-breaking mode, the impinging airflow and the buffering airflow are alternately generated, and a number of alternations is not smaller than two.

Optionally, a ratio of an airspeed of the impinging airflow to an airspeed of the atomizing airflow is not smaller than 1.1, and a ratio of an airspeed of the buffering airflow to the airspeed of the atomizing airflow is not greater than 0.5.

Optionally, the aroma diffuser includes a start-stop button and a controller, the start-stop button is configured to generate a working signal or a stop signal in response to a user operation, and the controller is configured to control the air delivery structure to enter the wall-breaking mode when receiving the working signal and enter the working mode after the wall-breaking mode ends, and to control the air delivery structure to stop the working mode when receiving the stop signal.

Optionally, the air delivery structure is further provided with a sweeping mode, when the air delivery structure is in the sweeping mode, a sweeping airflow is generated, an airspeed of the sweeping airflow is set such that the sweeping airflow takes the essential oil in the atomizing space away from the atomizing space without forcing the essential oil in the oil storage bottle to move towards the liquid outlet.

Optionally, a ratio of the airspeed of the sweeping airflow to the airspeed of the atomizing airflow is 0.3 to 0.5.

Optionally, the controller is configured to control the air delivery structure to stop the working mode and start the sweeping mode when receiving the stop signal, and a duration of the sweeping mode is not less than 5 seconds.

Optionally, the aroma diffuser further includes a wall-breaking button, the wall-breaking button is configured to generate a wall-breaking signal in response to a user operation, and the controller is configured to receive the wall-breaking signal and control the air delivery structure to enter the wall-breaking mode.

Optionally, the aroma diffuser includes a tubular atomizing chamber, two ends of the atomizing chamber define an air inlet and an atomizing port, respectively, the atomizing chamber is in communication with the oil delivery pipe and an internal space of the atomizing chamber is the atomizing space, the air inlet is in communication with the air delivery structure to access the atomizing airflow, the sweeping airflow, the impinging airflow or the buffering airflow, and the atomizing airflow, the sweeping airflow, the impinging airflow or the buffering airflow leaves the atomizing chamber through the atomizing port.

Optionally, the aroma diffuser further includes an expansion chamber in communication with the atomizing chamber, the expansion chamber is in a tubular shape, and a tube diameter of the expansion chamber is set to be gradually increased in a direction away from the atomizing port.

With the aroma diffuser provided by the present application, the air delivery structure alternately generates the impinging airflow and the buffering airflow, or alternately generates the buffering airflow and the impinging airflow, the surface tension of the essential oil remaining in the atomizing space and in the oil pipe wall of the oil delivery pipe can be broken through, and the remaining essential oil can be taken away from the atomizing space and the pipe wall of the oil delivery pipe, so as to achieve the effect of removing the residual essential oil and avoiding the accumulation of the essential oil to form a passivation layer, the problem of poor atomization effect of the existing aroma diffuser when used for a long time can be solved, thereby ensuring the performance of the aroma diffuser, and improving the service life of the aroma diffuser.

BRIEF DESCRIPTION OF THE DRAWINGS

In order to more clearly illustrate the technical solutions in the embodiments of the present application, the accompanying drawings that need to be used in the description of the embodiments or the prior art will be briefly introduced below. Obviously, the drawings in the following description are only some embodiments of the present application. For those of ordinary skill in the art, other drawings can be obtained from these drawings without paying creative work.

FIG. 4 is a second operational flowchart of an aroma diffuser according to an embodiment of the present application.

THE REFERENCE SIGNS IN THE FIGURES

Figure 1:
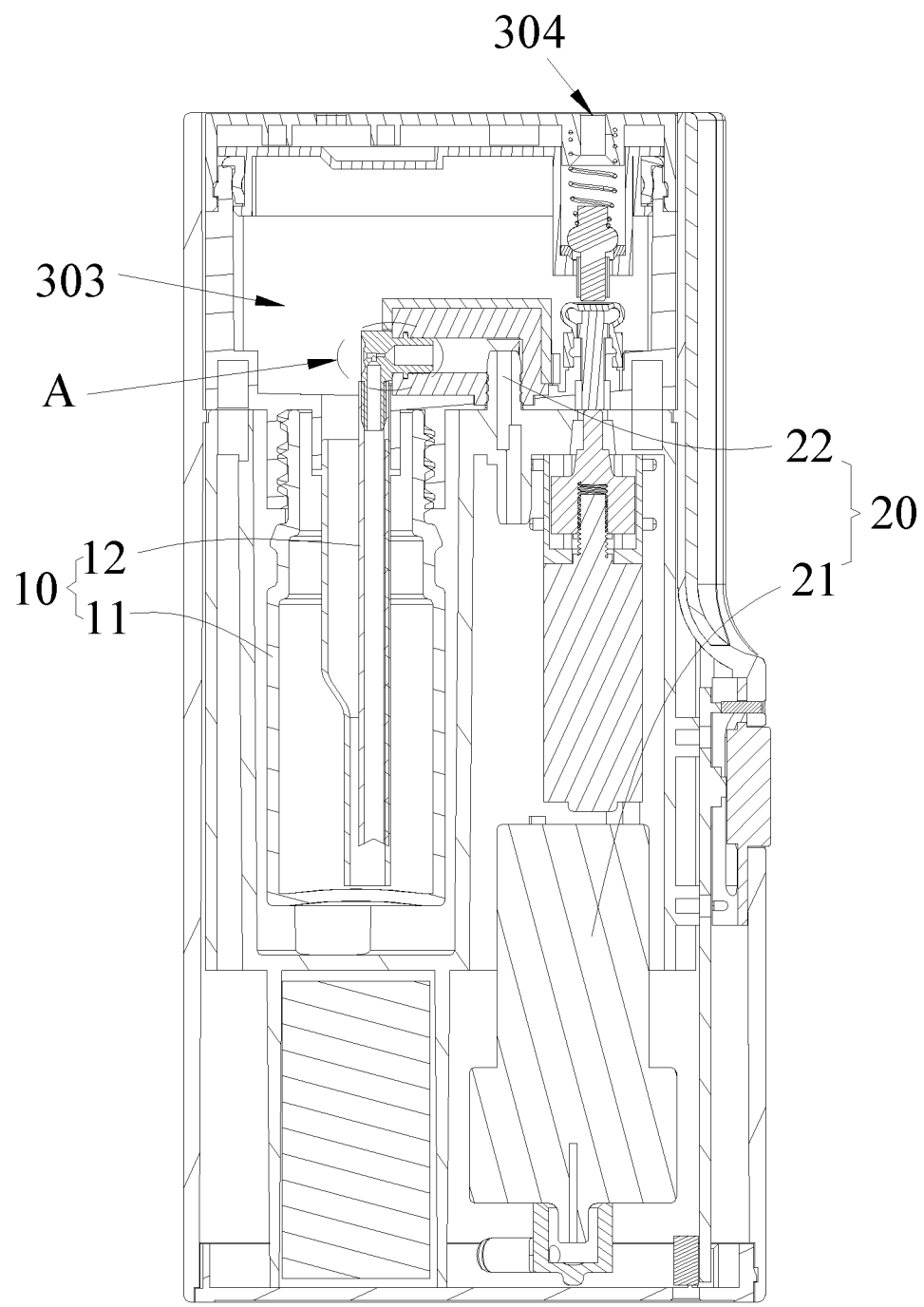
FIG. 1 is a cross-sectional view of an aroma diffuser according to an embodiment of the present application.

10—Oil supply structure;
11—Oil storage bottle;
12—Oil delivery pipe;
20—Air delivery structure;
21—Air pump;
22—Air delivery pipe;
301—Atomizing space;
302—Expansion chamber;
303—Diffusion chamber;
304—through hole.

DETAILED DESCRIPTION

In order to make the technical problems to be solved by the present application, the technical solutions, and the beneficial effects clearer, the present application will be further described in detail below with reference to the accompanying drawings and the embodiments. It should be understood that the specific embodiments described here are only used to explain the present application, but are not intended to limit the present application.

It should be understood that the orientations or positional relationships indicated by the terms "upper", "lower", "front", "rear", "inner", "outer", etc. are based on the orientations or positional relationships shown in the drawings, are only used for the convenience of describing the present application and simplifying the description, rather than indicating or implying that the device or element referred to must have a specific orientation, and be configured and operated in a specific orientation, and therefore cannot be understood as a limitation of the present application.

Referring to FIG. 1 to FIG. 4, an exemplary description of an aroma diffuser provided by the present application is provided.

Figure 2:
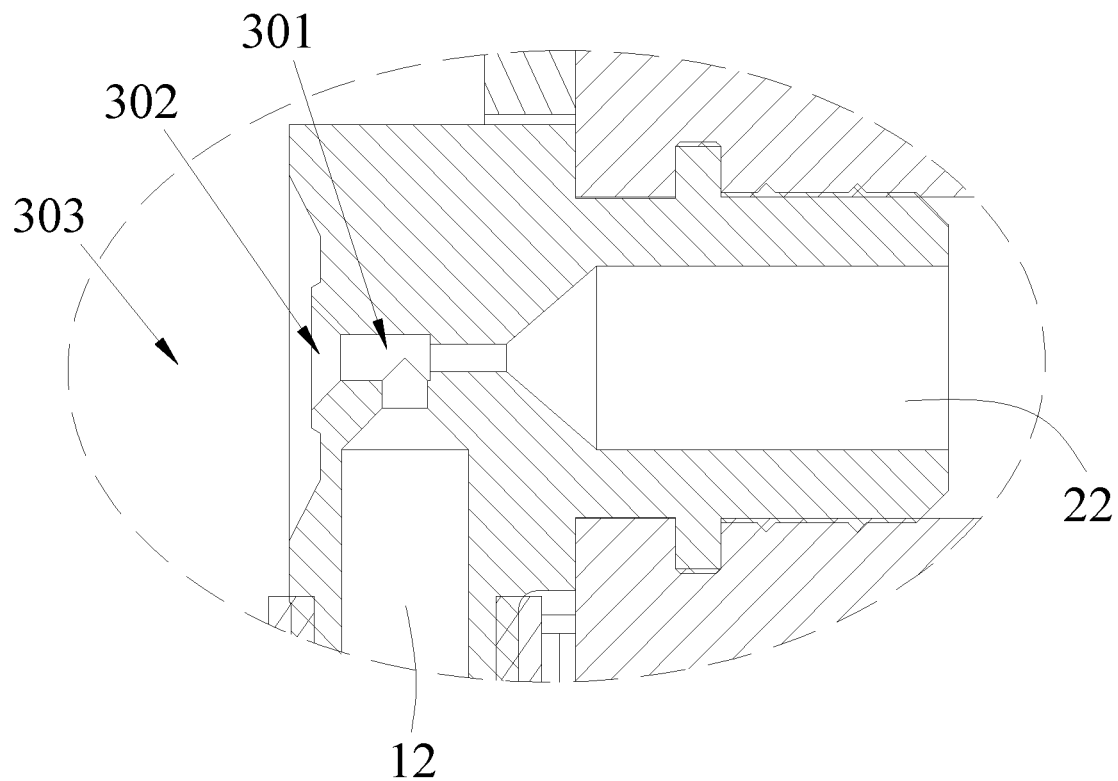
FIG. 2 is a partial enlarged view of part A in FIG. 1.

Referring to FIG. 1 and FIG. 2, the aroma diffuser includes an oil supply structure 10 and an air delivery structure 20.

The oil supply structure 10 includes an oil storage bottle 11 configured for accommodating essential oil and an oil delivery pipe 12 connected to the oil storage bottle 11. The oil delivery pipe 12 has a liquid outlet for the essential oil to flow out. The end side of the oil delivery pipe 12 is provided with an atomizing space 301.

The air delivery structure 20 includes an air pump 21 and an air delivery pipe 22. The air pump 21 drives the air to enter the atomizing space 301 through the air delivery pipe 22 to form a high-speed airflow. The moving direction of the high-speed airflow in the atomizing space 301 is perpendicular to the opening direction of the liquid outlet. In this embodiment, the airflow is defined as atomizing airflow, impinging airflow, buffering airflow, sweeping airflow, etc., according to the speed or pressure of the airflow.

The air delivery structure 20 has a working mode and a wall-breaking mode. When the air delivery structure 20 is in the working mode, an atomizing airflow is generated. The atomizing airflow passes by the liquid outlet and generates a negative pressure at the liquid outlet that forces the essential oil to enter the atomizing space 301. The essential oil in the oil storage bottle 11 enters the atomizing space 301 through the liquid outlet of the oil delivery pipe 12 under the action of negative pressure, and is sheared by the atomizing airflow to form a granular atomization state, and is sprayed forward with the atomizing airflow. In the structure shown in FIG. 1, the atomized essential oil leaves the atomizing space 301 with the atomizing airflow and enters the diffusion chamber 303, and then diffuses outward via the through hole 304 defined on the housing of the aroma diffuser.

When the air delivery structure 20 is in the wall-breaking mode, it alternately generates an impinging airflow and a buffering airflow or alternately generates a buffering airflow and an impinging airflow. The impinging airflow flows through the atomizing space 301 and can break through the surface tension of the essential oil. The buffering airflow flows through the atomizing space 301, the buffering airflow cannot force the essential oil in the oil storage bottle 11 to move to the atomizing space 301 and can take the essential oil in the atomizing space 301 away from the atomizing space 301. It can be understood that the airspeed of the impinging airflow is greater than that of the atomizing airflow, and the impinging airflow can break through the surface tension of the essential oil, such that the essential oil remaining in the atomizing space 301 is dispersed to form small particles and leaves the atomizing space 301 with the impinging airflow. In other words, the impinging airflow can hinder the accumulation of the essential oil and prevent the essential oil from forming a passivation layer in the atomizing space 301. In addition, the negative pressure generated by the impinging airflow at the liquid outlet is greater than the negative pressure generated by the atomizing airflow, such that more essential oil attached to the inner side of the oil delivery pipe 12 is sucked into the atomizing space 301 and chopped up for atomization, thereby preventing the essential oil from accumulating on the pipe wall of the oil delivery pipe 12 to form a passivation layer. From the above, by setting the impinging airflow, the deterioration of the atomization effect of the aroma diffuser caused by long-term use can be improved. The buffering airflow flows through the atomizing space 301, and the airspeed of the buffering airflow is smaller than that of the atomizing airflow, and it is difficult to force the essential oil in the oil storage bottle 11 to move to the liquid outlet. In this case, the essential oil in the oil delivery pipe 12 falls back into the oil storage bottle 11 under the action of gravity. The buffering airflow takes the essential oil remaining in the atomizing space 301 away from the atomizing space 301, so as to achieve a sweeping effect. In addition, the buffering airflow and the impinging airflow are alternately provided, including two situations: the buffering airflow is generated first and then the impinging airflow is generated, or the impinging airflow is generated first and then the buffering airflow is generated. Preferably, the impinging airflow is generated first and then the buffering airflow is generated, and the number of alternations is not less than two. The negative pressure generated by the impinging airflow will force the essential oil to move up to the atomizing space 301, such that when the impinging airflow is uninterrupted, the essential oil will move up to the atomizing space 301 uninterrupted, and after the impinging airflow ends, it is possible that there is still some essential oil remaining in the atomizing space 301. At this time, the buffering airflow flows through the atomizing space 301 and can take the essential oil remaining in the atomizing space 301 away from the atomizing space 301. In addition, after the buffering airflow ends, the essential oil in the oil delivery pipe 12 is in the state of falling back into the oil bottle 11, while the space in the oil delivery pipe 12 is filled with air. At this time, the impinging airflow is generated again to pass through the atomizing space 301. On the one hand, at the moment the impinging airflow just passes through the atomizing space 301, the essential oil in the oil storage bottle 11 has not moved upward yet, and the negative pressure generated by the impinging airflow can act on the pipe wall of the oil delivery pipe 12 to remove the essential oil adhered to the pipe wall of the oil delivery pipe 12. On the other hand, the essential oil in the oil storage bottle 11 has not yet entered the atomizing space 301, and the impinging airflow can directly act on the atomizing space 301 to remove the essential oil attached to the atomizing space 301, thereby enhancing the effect of removing the passivation layer.

To sum up, with the aroma diffuser provided by this embodiment, the problem of poor atomization effect of the existing aroma diffuser when used for a long time can be solved, thereby ensuring the performance of the aroma diffuser, and improving the service life of the aroma diffuser.

In this embodiment, the alternating times of the impinging airflow and the buffering airflow are two times. It can be understood that when the air delivery structure 20 is in the wall-breaking mode, the more the alternating times of the impinging airflow and the buffering airflow, the better the cleaning effect of the essential oil. Those of ordinary skill in the art can set the alternating times of the impinging airflow and the buffering airflow to be two times, three times, five times, etc., according to actual needs, which is not limited here.

Preferably, the ratio of the airspeed of the impinging airflow to the airspeed of the atomizing airflow is not smaller than 1.1, and the ratio of the airspeed of the buffering airflow to the airspeed of the atomizing airflow is not greater than 0.5. After many tests, the passivation layer of the essential oil can be effectively removed by setting the difference in airspeed between impinging airflow, atomizing airflow and buffering airflow. According to actual experiments, when the ratio of the airspeed of the impinging airflow to the airspeed of the atomizing airflow is greater than 1.1, and the ratio of the airspeed of the buffering airflow to the airspeed of the atomizing airflow is smaller than 0.5, and the alternating times of the impinging airflow and the atomizing airflow are two times, 95% of the essential oil remaining in the atomizing space 301 can be removed and 93% of the essential oil remaining on the pipe wall of the oil delivery pipe 12 can be removed. Those of ordinary skill in the art can further set the airspeed ratio of the impinging airflow to the atomizing airflow to be 1.1, 1.16, 1.18, 1.2, 1.25, 1.3, 1.5, etc., and set the airspeed ratio of the buffering airflow to the atomizing airflow to be 0.35, 0.4, 0.42, 0.45, 0.48, 0.5, etc., which are not limited here. It can be understood that when the structure of the air delivery pipe 22 is fixed, the airspeed of the high-speed airflow can be adjusted by adjusting the operating power of the air pump 21.

Figure 3:
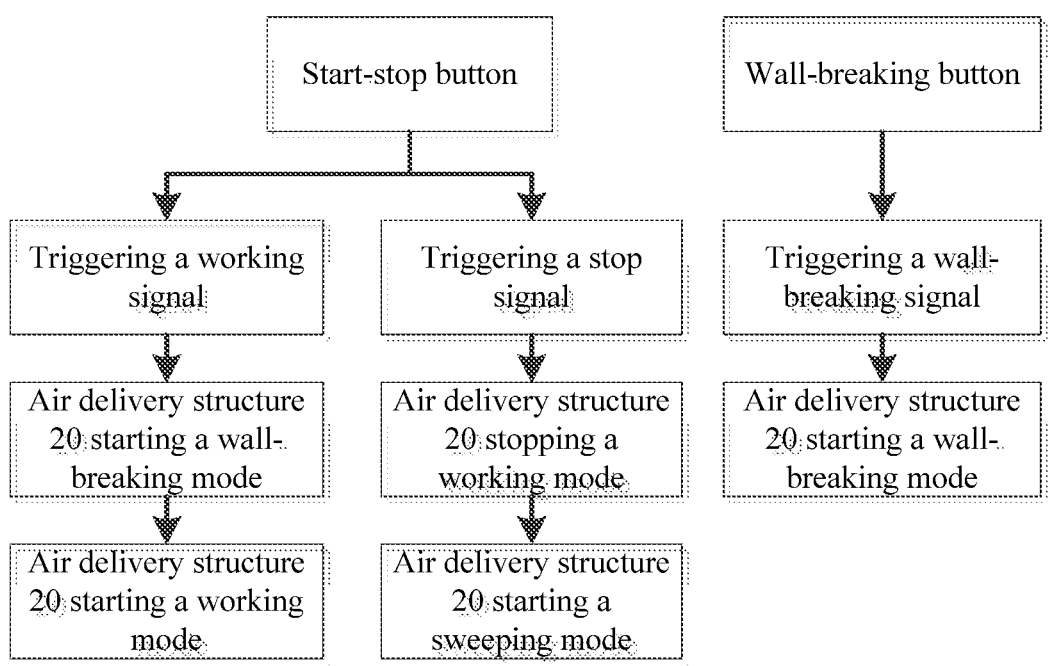
FIG. 3 is a first operational flowchart of an aroma diffuser according to an embodiment of the present application.

In another embodiment of the present application, referring to FIG. 3, the aroma diffuser includes a start-stop button and a controller. The start-stop button is configured to generate a working signal or a stop signal in response to a user operation, and the controller is configured to control the air delivery structure 20 to enter a wall-breaking mode when receiving a working signal and enter a working mode after the wall-breaking mode ends, and to control the air delivery structure 20 to stop the working mode when receiving a stop signal. When the aroma diffuser is turned on, the air delivery structure 20 first enters the wall-breaking mode and then enters the working mode. The oil delivery pipe 12 and the atomizing space 301 are cleaned first, so as not to hinder the subsequent atomization work.

The wall-breaking mode can also be activated separately. Specifically, referring to FIG. 3, the aroma diffuser also includes a wall-breaking button. The wall-breaking button generates a wall-breaking signal in response to a user operation. The controller is configured to receive a wall-breaking signal and to control the air delivery structure 20 to enter a wall-breaking mode. It can be understood that the activation of the wall-breaking button can occur separately after the aroma diffuser is powered on, and the user can independently trigger the wall-breaking signal to initiate the wall-breaking mode of the air delivery structure 20 without triggering a working signal. Referring to FIG. 4, the activation of the wall-breaking button can also occur when the air delivery structure 20 is in the working mode, at this time, the wall-breaking button is triggered to generate a wall-breaking signal, and the controller controls the air delivery structure 20 to suspend the working mode and enter the wall-breaking mode when the controller receives the wall-breaking signal, and the working mode is continued after the wall-breaking mode ends.

In other embodiments, when the aroma diffuser is activated, the wall-breaking signal may be triggered in a timing manner to make the air delivery structure 20 enter the wall-breaking mode.

Those of ordinary skill in the art can set the operating frequency of the wall-breaking mode according to actual needs, so as to achieve a better cleaning effect.

In another embodiment of the present application, referring to FIG. 3 or FIG. 4, the air delivery structure 20 also has a sweeping mode. When the air delivery structure 20 is in the sweeping mode, a sweeping airflow is generated. The airspeed of the sweeping airflow cannot force the essential oil in the oil storage bottle 11 to move towards the liquid outlet, and can take the essential oil in the atomizing space 301 away from the atomizing space 301. Preferably, the sweeping mode occurs after the air delivery structure 20 stops the working mode. Specifically, the controller controls the air delivery structure 20 to stop the working mode and start the sweeping mode when receiving a stop signal, and the sweeping mode lasts for no less than 5 seconds. When the atomizing space 301 is relatively large, the duration of the sweeping mode should be appropriately increased to facilitate the discharge of the essential oil in the atomizing space 301.

The sweeping airflow flows through the atomizing space 301, and its airspeed is smaller than that of the atomizing airflow, and it is difficult to force the essential oil in the oil storage bottle 11 to move to the liquid outlet. In this case, the essential oil in the oil delivery pipe 12 falls back into the oil storage bottle 11 under the action of gravity. The sweeping airflow takes the essential oil remaining in the atomizing space 301 away from the atomizing space 301 to achieve a sweeping effect.

In this embodiment, the ratio of the airspeed of the sweeping airflow to the airspeed of the atomizing airflow is 0.3-0.5. This pressure difference can take most of the essential oil in the atomizing space 301 away from the atomizing space 301. The airspeed of the sweeping airflow and the airspeed of the buffering airflow may be the same or different. Generally speaking, the airspeed of the sweeping airflow is not greater than the airspeed of the buffering airflow.

In another embodiment of the present application, referring to FIG. 1 and FIG. 2, the aroma diffuser has a tubular atomizing chamber. The two ends of the atomizing chamber are respectively an air inlet and an atomizing port. The atomizing chamber communicates with the oil delivery pipe 12, such that the internal space of the atomizing chamber is the atomizing space 301. The air inlet is in communication with the air delivery structure 20 to access the atomizing airflow, the sweeping airflow, the impinging airflow or the buffering airflow, and the atomizing airflow, the sweeping airflow, the impinging airflow or the buffering airflow leaves the atomizing chamber through the atomizing port.

By setting the atomizing chamber, a boundary for the atomizing space 301 is provided. The atomizing chamber is the flow channel of the gas mixed with the high-speed airflow and the essential oil. The atomizing chamber can block the outside air from entering the flow channel, thereby preventing the outside air from entering the flow channel to generate local turbulence and slow the speed of high-speed airflow. Under the action of the air pump 21 with the same power, compared with the setting of an open atomizing space 301 (the oil nozzle and the air nozzle are relatively independent, and the high-speed airflow from the air nozzle flows through the atomizing space 301 above the oil nozzle), the setting of a relatively closed atomizing chamber can improve the overall airspeed of the atomizing airflow in the atomizing space 301, and make the essential oil more easily disperse into smaller particles to improve the atomization effect, by increasing the overall airspeed of the impinging airflow and the buffering airflow in the atomizing space 301, it is beneficial to improve the cleaning effect, and by increasing the overall airspeed of the sweeping airflow in the atomizing space 301, the sweeping effect can be improved.

In another embodiment of the present application, referring to FIG. 2, the aroma diffuser further includes an expansion chamber 302 in communication with the atomizing chamber. The expansion chamber 303 is in a tubular shape, and the tube diameter of the expansion chamber is set to be gradually increased in the direction away from the atomizing port. The essential oil is mixed with the atomizing airflow in the atomizing chamber and atomized for the first time, and then further mixed and atomized in the expansion chamber 302 with the increase of the tube diameter, finally the essential oil leaves the expansion chamber 302 and enters the outside air or chamber (in the structure shown in the figure, the essential oil is mixed with the atomizing airflow, and then enters the diffusion chamber 303 from the expansion chamber 302, and is finally diffused outward via the through hole 304 arranged on the housing of the aroma diffuser), and is atomized again with the further expansion of the space. To sum up, the essential oil can be atomized three times to form smaller particles, thereby improving the atomization effect of the essential oil.

The above embodiments are only preferred embodiments of the present application, and are not intended to limit the present application. Any modification, equivalent replacement, and improvement made within the spirit and principle of the present application shall be included in the protection scope of the present application.

What is claimed is:

1. An aroma diffuser, comprising:
    an oil supply structure, comprising an oil storage bottle configured for containing an essential oil and an oil delivery pipe connected to the oil storage bottle, wherein the oil delivery pipe comprises a liquid outlet for the essential oil to flow out, and an end side of the oil delivery pipe is provided with an atomizing space; and
    an air delivery structure, provided with a working mode and a wall-breaking mode, wherein
        when the air delivery structure is in the working mode, an atomizing airflow is generated, the atomizing airflow passes by the liquid outlet, a negative pressure is formed at the liquid outlet, and the negative pressure forces the essential oil to enter the atomizing space; and
        when the air delivery structure is in the wall-breaking mode, an impinging airflow and a buffering airflow are alternately generated, or a buffering airflow and an impinging airflow are alternately generated, the impinging airflow flows through the atomizing space and breaks through a surface tension of the essential oil, the buffering airflow flows through the atomizing space, and the buffering airflow takes the essential oil in the atomizing space away from the atomizing space in the absence of forcing the essential oil in the oil storage bottle to move to the atomizing space.

2. The aroma diffuser according to claim 1, wherein when the air delivery structure is in the wall-breaking mode, the impinging airflow and the buffering airflow are alternately generated, and a number of alternations is not smaller than two.

3. The aroma diffuser according to claim 1, wherein a ratio of an airspeed of the impinging airflow to an airspeed of the atomizing airflow is not smaller than 1.1, and a ratio of an airspeed of the buffering airflow to the airspeed of the atomizing airflow is not greater than 0.5.

4. The aroma diffuser according to claim 1, wherein the aroma diffuser comprises a start-stop button and a controller, the start-stop button is configured to generate a working signal or a stop signal in response to a user operation, and the controller is configured to control the air delivery structure to enter the wall-breaking mode when receiving the working signal and enter the working mode after the wall-breaking mode ends, and to control the air delivery structure to stop the working mode when receiving the stop signal.

5. The aroma diffuser according to claim 4, wherein the air delivery structure is further provided with a sweeping mode, when the air delivery structure is in the sweeping mode, a sweeping airflow is generated, an airspeed of the sweeping airflow is set such that the sweeping airflow takes the essential oil in the atomizing space away from the atomizing space without forcing the essential oil in the oil storage bottle to move towards the liquid outlet.

6. The aroma diffuser according to claim 5, wherein a ratio of the airspeed of the sweeping airflow to the airspeed of the atomizing airflow is 0.3 to 0.5.

7. The aroma diffuser according to claim 6, wherein the controller is configured to control the air delivery structure to stop the working mode and start the sweeping mode when receiving the stop signal, and a duration of the sweeping mode is not less than 5 seconds.

8. The aroma diffuser according to claim 4, wherein the aroma diffuser further comprises a wall-breaking button, the wall-breaking button is configured to generate a wall-breaking signal in response to a user operation, and the controller is configured to receive the wall-breaking signal and control the air delivery structure to enter the wall-breaking mode.

9. The aroma diffuser according to claim 1, wherein the aroma diffuser comprises a tubular atomizing chamber, two ends of the atomizing chamber define an air inlet and an atomizing port, respectively, the atomizing chamber is in communication with the oil delivery pipe and an internal space of the atomizing chamber is the atomizing space, the air inlet is in communication with the air delivery structure to access the atomizing airflow, the impinging airflow or the buffering airflow, and the atomizing airflow, the impinging airflow or the buffering airflow leaves the atomizing chamber through the atomizing port.

10. The aroma diffuser of claim 9, wherein the aroma diffuser further comprises an expansion chamber in communication with the atomizing chamber, the expansion chamber is in a tubular shape, and a tube diameter of the expansion chamber is set to be increased in a direction away from the atomizing port.

11. The aroma diffuser according to claim 5, wherein the aroma diffuser comprises a tubular atomizing chamber, two ends of the atomizing chamber define an air inlet and an atomizing port, respectively, the atomizing chamber is in communication with the oil delivery pipe and an internal space of the atomizing chamber is the atomizing space, the air inlet is in communication with the air delivery structure to access the atomizing airflow, the sweeping airflow, the impinging airflow or the buffering airflow, and the atomizing airflow, the sweeping airflow, the impinging airflow or the buffering airflow leaves the atomizing chamber through the atomizing port.

12. The aroma diffuser of claim 11, wherein the aroma diffuser further comprises an expansion chamber in communication with the atomizing chamber, the expansion chamber is in a tubular shape, and a tube diameter of the expansion chamber is set to be increased in a direction away from the atomizing port.

* * * * *